(12) United States Patent
Balmer

(10) Patent No.: US 6,475,432 B2
(45) Date of Patent: Nov. 5, 2002

(54) CARRIER AND SUPPORT FOR WORK PIECES

(75) Inventor: Victor J. Balmer, Lake San Marcos, CA (US)

(73) Assignee: Ion Beam Applications, Inc., Oak Brook, IL (US)

(*) Notice: Subject to any disclaimer, the term of this patent is extended or adjusted under 35 U.S.C. 154(b) by 0 days.

(21) Appl. No.: 09/826,978

(22) Filed: Apr. 5, 2001

(65) Prior Publication Data

US 2002/0021981 A1 Feb. 21, 2002

Related U.S. Application Data

(60) Provisional application No. 60/225,287, filed on Aug. 15, 2000.

(51) Int. Cl.[7] ............................. A61L 2/00; A61N 5/00; B65D 21/00; B65D 6/28; B05C 13/00
(52) U.S. Cl. ..................... 422/22; 422/121; 422/306; 250/492.3; 250/453.11; 250/455.11; 206/509; 206/511; 206/562; 206/564; 206/712; 220/4.27; 118/500; 118/728; 156/345; 438/906
(58) Field of Search ........................ 420/1, 4–5, 21–24, 420/28, 121, 123, 292, 300, 302, 305–306, 903, 906–907, 940; 250/492.3, 453.11, 455.11; 206/712, 562, 564, 509, 511–512; 220/4.27; 118/500, 728; 156/345; 438/906; 134/901, 1, 1.3; 34/245–278

(56) References Cited

U.S. PATENT DOCUMENTS 4,350,578 A * 9/1982 Frieser et al.
5,191,224 A * 3/1993 Tazunoki et al.
5,701,031 A * 12/1997 Oguchi et al.
5,821,175 A * 10/1998 Engelsberg
5,844,683 A * 12/1998 Pavloski et al.
6,087,719 A * 7/2000 Tsunashima
6,152,075 A * 11/2000 Gardner et al.

FOREIGN PATENT DOCUMENTS

DE 33 42 104 A1 * 5/1985 ........... H01L/23/44

* cited by examiner

Primary Examiner—Robert J. Warden, Sr.
Assistant Examiner—Monzer R. Chorbaji
(74) Attorney, Agent, or Firm—Dorsey & Whitney LLP

(57) ABSTRACT

A device for use in carrying and supporting a work piece before, during, and after a treatment process. The device can be used for both shipping and treating the work piece, and the device will not adversely affect the work piece during the treatment process. The device comprises at least one plate which has at least one relieved region for holding a work piece. The plate has a density the same as or very similar to the density of the work piece, so that the plate and work piece together have a substantially uniform density.

17 Claims, 4 Drawing Sheets

SteriGenics proposed design

CARRIER AND SUPPORT FOR WORK PIECES

This application claims benefit from prior Provisional Application Serial No. 60/225,287, filed Aug. 15, 2000.

BACKGROUND

The present invention relates to containers and supports for carrying, containing and/or supporting a work piece or work pieces, including containing and/or supporting a work piece or work pieces during a work piece treatment process and during shipment to and from a treatment process site.

Radiation processing is a widely used method of commercial sterilization. In particular, gamma and electron beam radiation are widely used. Both methods are prominent within the industry for the sterilization of health care products, while electron beam processing holds a large size of the market for raw materials and products such as commercial polymers and gem stones.

Gamma radiation has long been recognized as a safe, cost competitive method for the sterilization of health care products, components and packaging. Gamma radiation, a form of pure energy which is generally characterized by deep penetration of low dose rates, effectively kills microorganisms throughout a subject product and its packaging with very little temperature effect. Some advantages of gamma radiation are precision dosing, rapid processing, uniform dose distribution, system flexibility and immediate availability of product after processing through dosimetric release. Gamma radiation is a penetrating sterilant. No area of the product, or its components, is left with uncertain sterility after treatment. Packaging remains intact with gamma processing because there is no requirement for pressure and vacuum seals are not stressed. In addition, gamma radiation eliminates the need for permeable packaging materials.

Electron beam (e-beam) radiation is a form of ionizing radiation that can be an effective means of destroying microorganisms. E-beam irradiation, generally characterized by low penetration and high dose rates, is a process by which products are exposed to a concentrated, high current stream of electrons generated by accelerators that produce a beam that is either pulsed or continuous. A work piece or subject material absorbs energy from the electrons as it passes beneath or in front of the electron beam. E-beam irradiation is mostly used in the health care products market for processing of high volume, low value products such as syringes, and for low volume, high value products such as cardio-thoracic devices.

The energy absorbed per unit mass of material processed by radiation is referred to as the absorbed dose and is identified as either a kilo Gray (kGy) or Megarad (Mrad) unit of measure. This absorption alters various chemical and biological bonds, and it is this absorption of energy or dose delivery that destroys the reproductive cells of microorganisms. The accompanying table, labeled Table A, provides a comparison of sterilization methods, including some of the parameters or factors in selecting one of the methods. Commercial e-beam accelerators range in energies from 3 MeV to 12 MeV (million electron volts) and usually operate at a single energy.

Typically, high energy electron beams are needed for sterilization of health care products to achieve penetration of product and packaging. Product density, size and orientation of packaging must be considered when evaluating e-beam sterilization. In general, e-beam irradiation performs best when used on low density, uniform and uniformly packaged products. E-beam sterilization requires the simultaneous control of the beam's current, scan width and energy, as well as the speed and/or time of exposure, e.g., control of the speed of a conveyor transporting a product through a beam. Speed of the conveyor may be regulated with feed back circuitry from the beam current. If the beam current changes during processing, the conveyor speed correspondingly changes to insure that the delivered dose is held constant.

There are problems, however, currently associated with radiation processing regardless of the type of radiation. First, radiation treatment of work pieces in containers of materials different than that of the work piece may cause the work pieces to have a greater absorbed dose variation. A dissimilar support plate or packaging material can reduce the energy of the penetrating electrons by varying amounts and create a non-uniform dose absorption over the surface area or throughout the thickness of the work piece. In addition, out-gassing from dissimilar support plates and packaging materials causes contamination of the work piece. Finally, work pieces are often manually placed onto and removed from conveyor systems. Handling work pieces in this manner can cause contamination or damage to the work piece.

Accordingly, it would be advantageous to provide a device for use in carrying and/or supporting work pieces to be subjected to e-beam radiation, or other treatments, before, during and after the treatments, wherein the device improves or at least does not adversely impact the efficacy of the e-beam or other treatment.

SUMMARY

The present invention is a carrying and support device that will not adversely affect work pieces when subjected to e-beam radiation or other treatments. Specifically, the present invention will reduce or eliminate the amount of out-gassing from dissimilar materials and minimize the absorbed dose variation within the work pieces. The present invention relates to an apparatus for minimizing the amount of out-gassing and absorbed dose variation, as well as a method for sterilizing or otherwise treating a work piece wherein there is little or no out-gassing and a minimum amount of absorbed dose variation.

More specifically, the carrying and support device of the present invention comprises at least one plate which has at least one relieved region for holding a work piece. The plate has a density the same as or very similar to the density of the work piece, so that the plate and work piece together have a substantially uniform density. In addition, in some embodiments the plate can be used for packaging. The plate can be sent to a manufacturer, where the work piece is placed on or into the carrying and support device, without any additional packaging. The manufacturer would then send the entire unit to the treatment site where it is subjected to treatment. The entire unit, now containing a sterilized or otherwise treated work piece, is then sent back to the manufacturer.

The method of the present invention generally includes providing a work piece or work pieces and a support and carrying device having the same or similar density as the work pieces, placing the work pieces on or into the support and carrying device, and subjecting the entire unit to sterilization or other treatment.

Accordingly, an embodiment of the present invention provides a support and carrying device that will not adversely affect work pieces when those work pieces are shipped and/or subjected to commercial sterilization or other treatment.

Another embodiment of the present invention provides a support and carrying device that has a density the same as or very similar to the work pieces to be carried by the support and carrying device.

A further embodiment of the present invention provides a support and carrying device that will not adversely affect work pieces when subjected to treatment and can be used for packaging and shipment.

A still further embodiment of the present invention provides a method for sterilizing or otherwise treating work pieces where the work pieces are not adversely affected by out-gassing or radiation dose variation.

These and other features, aspects, and advantages of the present invention will become better understood with regard to the following description, appended claims, and accompanying drawings.

DETAILED DESCRIPTION

The present invention relates generally to a support and carrying device for work pieces. Specifically, the present invention can be used to support and carry work pieces to be subjected to radiation treatment, before, during and after treatment.

Any reference to front and back, right and left, top and bottom and upper and lower are intended for convenience of description, not to limit the present invention or its components to any one positional or spacial orientation.

Figure 1:
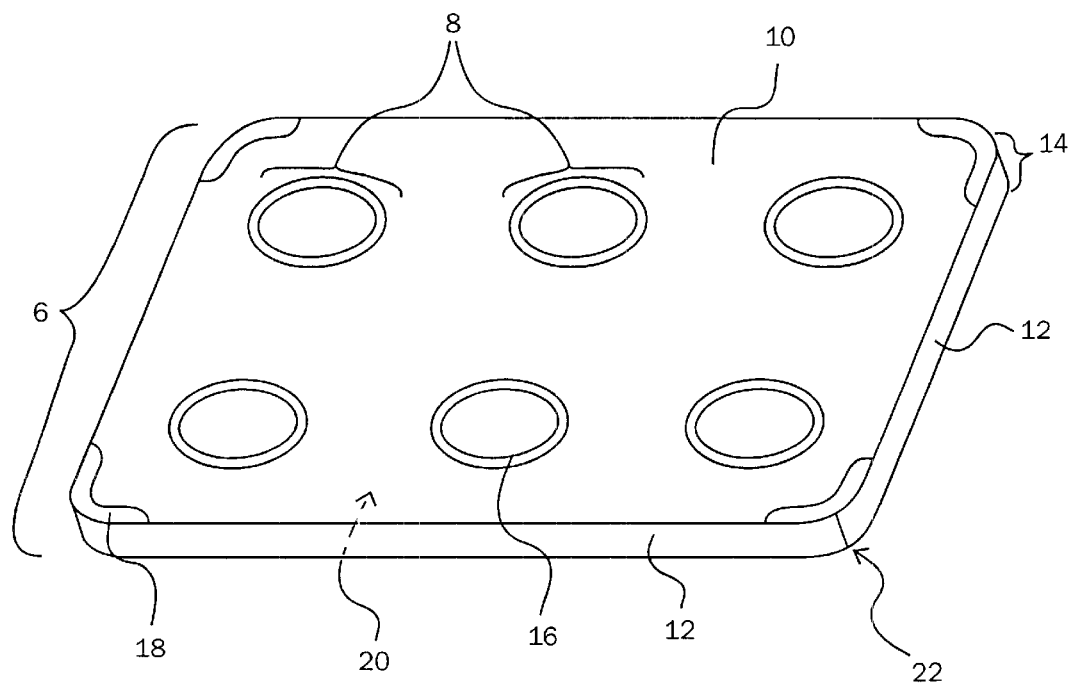
FIG. 1 is a top perspective view of one embodiment of the present invention.

One embodiment of the present invention is a single plate 6, as shown in FIG. 1. The receiving plate 6 of this embodiment is generally rectangular; however, the overall shape of the receiving plate 6 can be adapted to the particular needs of the work piece manufacturer. The receiving plate 6 has a selected number of relieved regions 8 for receiving work pieces. While the depicted relieved regions 8 are circular holes, it should be appreciated that the relieved regions 8 may have a selected shape adapted to receive work pieces of various complementary shapes. The relieved regions 8 have a lip 16 to support a work piece.

The receiving plate 6 has a top surface 10 and a bottom surface 20. Except for the relieved regions 8, the top surface 10 may be substantially continuous or, in other embodiments, may have additional relieved regions or holes for reducing the weight of the plate 6, or for shaping or modifying the transmission of the treatment of the selected treatment process. The top surface 10 may be adapted to have regions that are transparent, partially transparent and/or non-transparent to various forms of radiation techniques. The receiving plate 6 has side surfaces 12. The width 14 of the side surfaces 12 will vary depending on the work piece and the treatment process.

Figure 2:
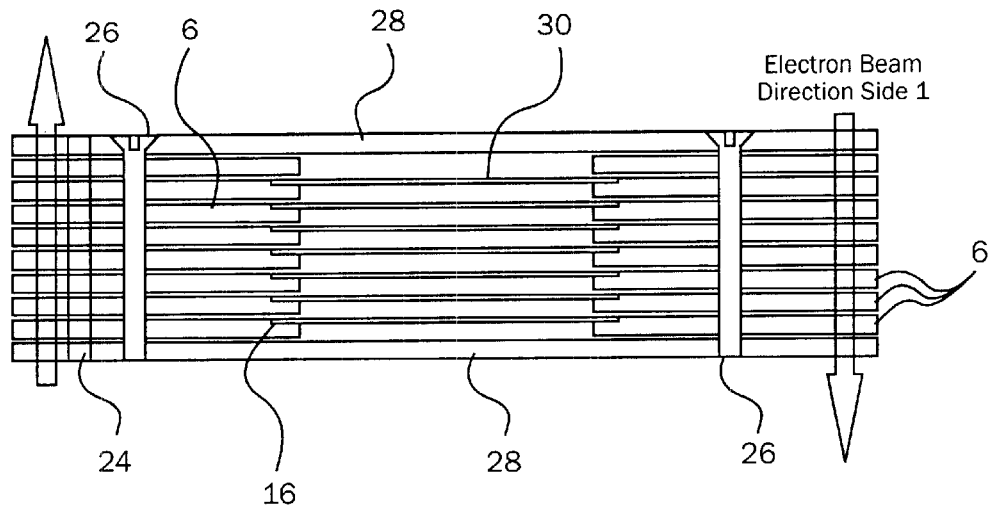
FIG. 2 is a cross-sectional view of one embodiment of the present invention, wherein an embodiment of the support device of the present invention may be combined or stacked for use in a method of treating work pieces.

In some embodiments, the top surface 10 has engagement elements 18 adapted to engage or contact other plates or plate edges for improving the plate-to-plate connection when the plates 6 are stacked or otherwise connected, as shown in FIG. 2. The bottom surface 20 has receiving elements 22 adapted to receive engagement elements 18. In alternative embodiments, the engagement elements could be located on the bottom surface 20, and the receiving elements could accordingly be located on the top surface 10. As shown, the engagement elements and receiving elements are located on the corners of receiving plate 6. Other embodiments are possible where receiving plates 6 have no corners, or where the engagement elements 18 and receiving elements 22 are located elsewhere on the receiving plates 6. In addition, other embodiments are possible where the plates 6 have no engagement elements or receiving elements.

FIG. 2 shows an embodiment of the present invention in which a plurality of the receiving plates 6 are stacked. In this embodiment, a top plate 28 and a bottom plate 28 are provided. The top and bottom plates have substantially continuous surfaces and are substantially the same shape as the receiving plates 6. The top and bottom plates 28 may or may not be transparent, opaque, or neutral to the treatment process. The top and bottom plates 28 and receiving plates 6 may have a plurality of threaded bores 24 (shown in phantom) extending through each of the plates. Suitable attachment members, e.g., screws 26 or the like, may be used to connect the plates 28 to form the stack.

Preferably, the top and bottom plates 28 and the receiving plates 6 are made of a material having the same or similar density as the work pieces. In the embodiment shown in FIG. 2, the work pieces 30 are silicon wafers. Accordingly, the top and bottom plates 28 and the receiving plates 6 are aluminum. It is also preferred that fastening means, in this embodiment screws, are made of a material having the same or similar density as the work pieces. The combination of the device of the present invention with the work pieces, as shown in FIG. 2, when placed in an irradiator, thus presents itself in a manner such that it is of uniform or near uniform density. This minimizes the variation in dose distribution throughout the combination.

Figure 3A:
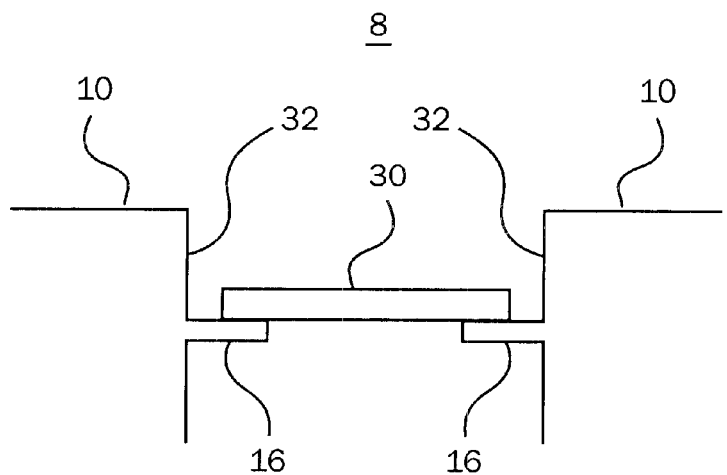
FIGS. 3a and 3b are cross-sectional views of embodiments of the present invention.
Figure 3B:
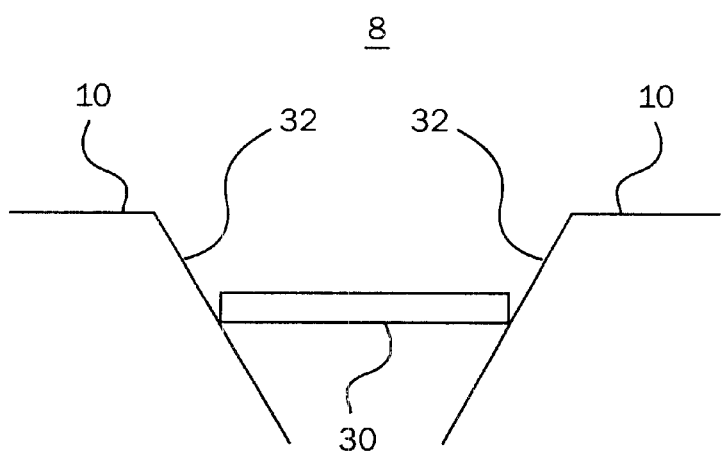

FIG. 3 shows top surface 10 having a relieved region 8. The relieved region 8 has an inner surface 32. As shown in FIG. 3, the inner surfaces are substantially perpendicular to each other, and the distance between them is slightly larger than the length of the work piece 30. Relieved region 8 has a lip 16 for supporting the work piece 30. Preferably, the lip 16, inner surface 32, and top surface 10 are permanently attach ed to one another, i.e., they are all one unit.

Alternatively, the lip 16 could be a separate piece fastened to the inner surface 32 by any suitable means. In the preferred embodiment, the lip 16 is one unit and runs continuously along the inner surface 32. Alternatively, the lip 16 could occupy only small sections along the inner surface 32, so long as there is enough lip to support the work piece 30. Preferably, the lip 16 is positioned deep enough into the relieved region 8 so that the entire work piece 30 lies within the relieved region 8.

FIG. 3a shows an alternative embodiment of the relieved region of the present invention. The relieved region of this embodiment has no lip 16. The inner surface 32 is angled in to create a funnel shape such that the inner surface 32 performs the function of the lip 16 of the preferred embodiment and supports the work piece 30.

Figure 4:
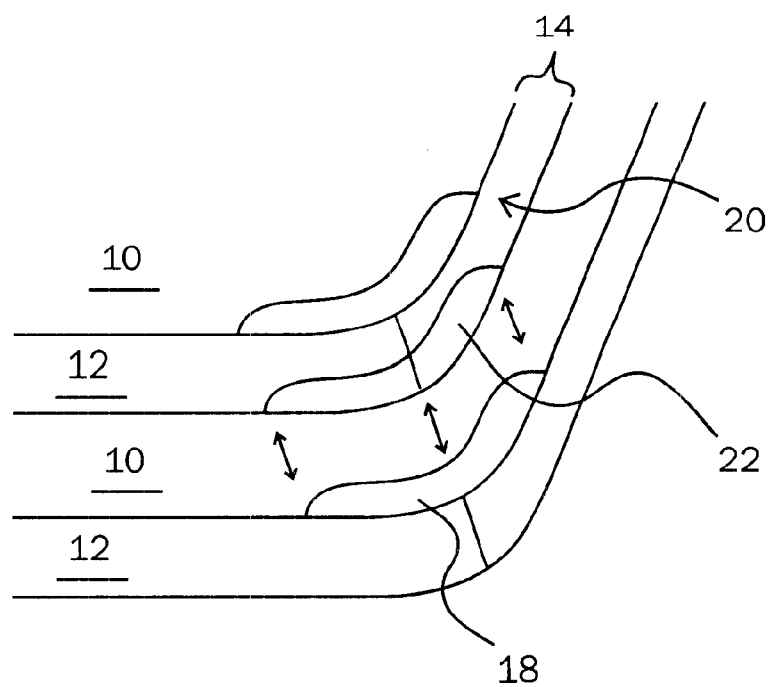
FIG. 4 depicts further details of the embodiment depicted in FIG. 2.

FIG. 4 shows an exemplary plate-to-plate connection of one embodiment of the present invention. Engagement element 18 is a raised portion along the outer edge of the top surface 10. Preferably, engagement element 18 is one piece with the rest of the receiving plate 6 and is made of the same material as the receiving plate 6. In this preferred embodiment, receiving element 22 is an open area the same shape and size as the engagement element and located on the bottom surface 20. The engagement element 18 is inserted into the receiving element 20 in an interlocking fashion. This interlocking connection prevents the plates from moving or sliding relative to each other.

In this embodiment, the engagement elements 18 are located along the corner of top surface 10. In alternative embodiments, the engagement elements 18 may be located anywhere on the top surface 10, so long as the complementary receiving elements 22 are located accordingly. In yet another embodiment, the engagement elements 18 are located on the bottom surface 20 while the receiving elements 22 are located on the top surface 10. The size of the engagement elements 18, and thus the receiving elements 22, is not important except that the engagement elements 18 should not be taller than the width 14 of the side surface 12.

Preferably, the entire device of the present invention, including all fastening means, is made of a material having the same or similar density as the work piece or pieces to be treated. This minimizes the amount of out-gassing and thus minimizes the contamination of the work piece. In addition, use of a support and carrying device having the same or similar density as the work piece minimizes the variation in dose distribution throughout a material or product to be treated. Optimally, the work piece plus device is subjected to double-sided irradiation. This further reduces the variation in dose distribution throughout a material or product to be treated. Attached Table A shows the relatively low dose variation when the device of the present invention is used to support and carry work pieces subject to irradiation.

Although the present invention has been described with reference to depicted exemplary embodiments, other versions are possible. Therefore, the spirit and scope of the present invention should be determined by reference to the appended claims.

What is claimed is:

1. A carrier and support device for use in radiation treatment processes, comprising:
    a plurality of stackable plates, each plate having a throughbore and having a lip adjacent to said throughbore for receiving a work piece, said work piece having a density, wherein said plate has generally the same density as the work piece, wherein a plurality of said workpieces can be simultaneously treated with radiation when the plurality of plates are stacked.

2. The carrier and support device of claim 1, wherein said plurality of plates each have edge portions adapted to engage other plates.

3. The carrier and support device of claim 2, further comprising:
    a stack of said plurality of plates, said stack comprising a top and a bottom plate, said top and bottom plates having substantially continuous surfaces.

4. The carrier and support device of claim 3, further comprising:
    a plurality of screws connecting said plurality of plates and said top and bottom plates.

5. The carrier and support device of claim 1, wherein said plate is made of aluminum and adapted to receive silicon wafers.

6. A carrier and support device for use in radiation processing, comprising:
    a plurality of plates having relieved regions for receiving work pieces, wherein said plates are made of aluminum and adapted to carry silicon wafers, said plates having edge portions adapted to engage other plates for plate-to-plate connection, said plates having a lip adjacent to said relieved regions; and
    a stack of said plurality of plates, said stack having a top and a bottom plate, said top and bottom plates having substantially continuous surfaces, wherein said silicon wafers can be substantially simultaneously treated with radiation when carried within said stacked plurality of plates.

7. A method of commercial sterilization, comprising the steps of:
    providing work pieces to be sterilized;
    providing a plurality of stackable plates, each plate having a for receiving work pieces; and
    subjecting the said plurality of stackable plates and the work pieces carried thereby to sterilization when said stackable plates are stacked together, wherein the at least one plate for receiving work pieces is made of a material having generally the same density as the work pieces.

8. The method of claim 7, wherein said sterilization is a treatment from the group consisting of electron beam radiation and gamma radiation.

9. The method of claim 7, wherein said sterilization is electron beam sterilization.

10. The method of claim 7, wherein the at least one plate and the work pieces carried thereby have a top side and a bottom side, wherein the at least one plate and the work pieces are subjected to sterilization treatment from points above and below said top and bottom sides, respectively.

11. The method of claim 7, wherein the at least one plate has edge portions adapted to engage other plates.

12. The method of claim 7, further comprising the steps of connecting and fastening said plates to each other using a plurality of screws.

13. A carrier and support device for use in radiation processing, comprising:
    a plurality of plates, each plate having relieved regions for receiving work pieces, said plates being substantially flat except for said relieved regions, said plates having four edges, wherein each edge is parallel to one other edge and perpendicular to the other two of said edges so that said edges form a shape that is substantially rectangular, wherein said edges are adapted for top to bottom plate-to-plate connection when said plates are stacked, said relieved regions having a shape substantially similar to that of said work pieces, wherein said relieved regions have a volume great enough to accommodate at least one of said work pieces, said work pieces having a density, wherein said plate has generally the same density as the density of the work pieces;

a lip adjacent to each of said relieved regions, wherein said lip is adapted to support said work pieces;

a stack of said plurality of plates, said stack having a top plate and a bottom plate, said top and bottom plates having substantially continuous surfaces, wherein said top and bottom plates are substantially the same shape and made of the same material as said plates for receiving work pieces;

a plurality of threaded bores extending through each of said top and bottom plates and said receiving plates; and a plurality of screws inserted through each of said bores and connecting said top and bottom plates and said receiving plates, wherein said work pieces are subjected to substantially simultaneous radiation processing when said stack is subjected to radiation processing.

14. A carrier and support device for use in a radiation treatment processes, comprising:

a plate having a plurality of throughbores, each throughbore having a lip for receiving and supporting a work piece so that workpiece is positioned with respect to the plate so that during sterilization for radiation uniform dosage is achieved throughout each workpiece, said work piece having a density, wherein said plate has generally the same density as the work piece.

15. The carrier and support device of claim 14, wherein said plate is made of aluminum and adapted to receive silicon wafers.

16. The carrier and support device of claim 14, further comprising:

a plurality of the plates, wherein said plates have edge portions adapted to engage other plates.

17. The carrier and support device of claim 16, further comprising:

a stack of said plurality of plates, said stack comprising a top and a bottom plate, said top and bottom plates having substantially continuous surfaces.

* * * * *